(12) United States Patent
Lee et al.

(10) Patent No.: US 6,894,073 B2
(45) Date of Patent: May 17, 2005

(54) USE OF DITERPENE COMPOUND AS A THERAPEUTIC AGENT OF INFLAMMATION, IMMUNE DISEASE OR CANCER

(75) Inventors: Jung-Joon Lee, Taejon-si (KR); Jeong-Hyung Lee, Taejon-si (KR); Hang-Sub Kim, Taejon-si (KR); Young-Soo Hong, Taejon-si (KR); Bang-Yeon Hwang, Taejon (KR)

(73) Assignee: Korea Research Institute of Bioscience and Biotechnology (KR)

( * ) Notice: Subject to any disclaimer, the term of this patent is extended or adjusted under 35 U.S.C. 154(b) by 5 days.

(21) Appl. No.: 10/450,217

(22) PCT Filed: Dec. 12, 2001

(86) PCT No.: PCT/KR01/02152

§ 371 (c)(1),
(2), (4) Date: Jun. 11, 2003

(87) PCT Pub. No.: WO02/47675

PCT Pub. Date: Jun. 20, 2002

(65) Prior Publication Data

US 2004/0048918 A1 Mar. 11, 2004

(30) Foreign Application Priority Data

Dec. 12, 2000 (KR) ......................................... 2000-75608

(51) Int. Cl.$^7$ .................... A61K 31/122; A61K 31/352; C07C 49/115; C07C 49/215; C07D 311/78
(52) U.S. Cl. ....................... 514/453; 514/680; 549/386; 568/326
(58) Field of Search ......................... 549/386; 568/326; 514/453, 680

(56) References Cited

FOREIGN PATENT DOCUMENTS

| JP | 57167938 | 10/1982 |
| JP | 9087189 | 3/1997 |

OTHER PUBLICATIONS

Yoshio Takeda et al., "Structural Elucidation of New Diterpenoids Isolated From *Rabdosia umbrosa* var. *leuchantha* f. Kameba", J. Chem. Soc. Perkin Trans., vol. 1, No. 11, 1987, p. 2403–2409.

Huang Danyang et al., "Crystal and Molecular Structure of Rabdoserrin–B", J.Struct. Chem., vol. 7, No. 1, 1988, p. 17–21.

Tetsuro Fujita, et al., "Cytotoxic and Anti–tumor Activities of Rabdosia Diterpenoids", *Planta Medica*, vol. 54, No. 5, 1988, p. 414–417.

Li Jicheng, et al., "The Structure of Henryin", ACTA Botanica Yunnanica, vol. 6, No. 4, 1984, p. 453–456.

*Primary Examiner*—Taofiq Solola
(74) *Attorney, Agent, or Firm*—Muserlian, Lucas and Mercanti (57) ABSTRACT

The disclosure concerns novel use of diterpene compound as a therapeutic agent of inlfammation, immune disease or cancer. More particularly, the present invention relates to novel use of diterpene compound that include kamebanin, kamebacetal A, kamebakaurin, and exisanin A, which would be effective for the treatment inflammation, immune disease or cancer by inhibiting the production of nitric oxide, prostaglandin, and TNF-$_{a1}$ through the suppression of NF-$_k$B activity.

7 Claims, 6 Drawing Sheets

USE OF DITERPENE COMPOUND AS A THERAPEUTIC AGENT OF INFLAMMATION, IMMUNE DISEASE OR CANCER

This patent application claims a benefit of priority from Korean Patent Application No. 2000-75608 filed Dec. 12, 2000, through PCT Application Ser. No. PCT/KR01/02152 filed Dec. 12, 2001, the contents of each of which is incorporated herein by reference.

FIELD OF THE INVENTION

The present invention relates to a novel use of diterpene compounds as a therapeutic agent for the treatment of inflammatory disease, immunological disease or cancer.

BACKGROUND OF THE INVENTION

Exposure of human tissue or cells to harmful stimuli such as lipopolysaccharide (LPS), inflammatory mediators, toxic chemicals, and radiation are known to activate immune cells to produce inflammatory mediators such as tumor necrosis factor-α (TNF-α), interleukin-1 (IL-1), IL-6, prostaglandin, leucotriene, and nitric oxide (NO). These event causes inflammatory diseases (e.g., arthritis and septic shock), immunological diseases (e.g., graft rejection, autoimmune disease, and diabetes mellitus), and the death of neuron cells.

Under normal condition, NO, an inflammatory mediator is produced in the endothelial cells and macrophages and shows various physiological activities including the induction of cell death, and antibacterial activity. Especially, NO is known to be involved in the maintenance of the homeostasis of blood pressure by the control of relaxation of endothelial cells in the blood vessel. The above-mentioned harmful stimuli (LPS, inflammatory mediators, and radiation exposure) can induce the expression of an inducible nitric oxide synthetase (iNOS), resulting in the overproduction of NO. It is the excessive production of NO that induces the above-mentioned diseases. Therefore, an inhibitor of iNOS activity can be a useful therapeutic agent against various inflammatory diseases.

Another inflammatory mediator, prostaglandin, such as $PGE_2$, PGF2a, and $PGI_2$, is a kind of hormone originating from arachidonic acid and involved in various physiological activities. Its production is regulated by cyclooxygenase (COX), a rate-determining enzyme in the production of prostaglandins. Non-steroidal anti-inflammatory and analgesic agent such as aspirin and indometacin, which inhibit the synthesis of prostaglandin by inhibiting COX activity, are known to show an excellent therapeutic effect for arthritis.

TNF-α, which is produced in the macrophages and fibroblasts upon activation by LPS and various inflammatory mediators, induces a cytotoxic effect as well as the production of prostaglandin and other cytokines such as IL-1 and IL-6. TNF-α was originally found as a tumor necrosis factor and was reported to be involved in various diseases, including autoimmune diseases (e.g., rheumatoid arthritis and graft rejection responses), allergic inflammatory diseases (e.g., asthma and atopic dermatitis), and acute immunological disorders (e.g., septic shock and acute liver disease). Therefore, the development of a compound inhibiting TNF-α production is under active investigation. According to recent studies, a mutant mouse having a defective TNF-α receptor is known to have resistance against toxic effects caused by LPS. In addition, a mouse treated with antibodies against TNF-α is known to have an effect on preventing arthritis and toxicity caused by LPS (B. Beutler, *Science*, 1985, 229, 869; K. Pfeffer et al., *Cell*, 1993, 73, 457).

Activation of nuclear factor κB (NF-κB) is required for the production of above mentioned NO, prostaglandins, and TNF-α. NF-κB is also known to regulate the expression of a variety of proteins involved in the various cellular responses such as apoptosis, immune responses, and inflammatory reactions.

NF-κB is composed either of homodimer or heterodimer of several proteins including p50 and p65 proteins and exists as inactive forms in the cytoplasm by binding with I-κB protein, the inhibitor of NF-κB. Stimulated by various stimuli such as TNF-α, IL-1, LPS, free radical, and irradiation, however, I-κB kinase (IKK) is activated and thus phosphorylates I-κB. As a result, NF-κB dissociates from I-κB, enters the nucleus, and regulates the expression of various genes involved in the inflammatory or immunological responses (P. A. Baeueric, D. Baltimore, *Cell*, 1996, 98, 13–20).

In addition NF-κB regulates not only the expression of COX-2, various cytokines including TNF-α, and adhesion molecules such as E-selection, I-CAM, and V-CAM, but also that of apoptosis signals through death receptors such as the TNF-α receptor family (F. H. Epstein, *New England Journal of Medicine*, 1997, 336(15), 1066–1071; T. Collins, M. A. Read et al., *FASEB J.*, 1995, 9, 899–909). For example, it is known that NK-κB plays an important role in the regulation of the expression of antiapoptotic proteins such as Mn-SOD, zinc finger protein (A20) and inhibitor of apoptosis protein (IAP), which are known to inhibit death receptor-mediated apoptosis process (D. J. Van Antwerp, S. J. Martin et al., *Trends in Cell Biology*, 1998, 8, 107–111; C.-Y. Wang, M. W. Mayo et al., *Science*, 1998, 281, 1680–1683). The treatment of a cancer cell with TNF-α or adriamycin induces the activation of NF-κB, which in turn results in the resistant of the cancer cell to TNF-α- or adriamycin-induced cytotoxicity and apoptosis. Therefore, if the activation of NF-κB is inhibited, the cytotoxic effect of anticancer drug increases by the inhibition of expression of antiapoptotic proteins (A. A. Beg, D. Baltimore, *Science*, 1996, 274, 782–784; C.-Y. Wang, M. W. Mayo, A. S. Baldwin Jr., *Science*, 1996, 274, 784–789).

Well known anti-inflammatory agents such as glucocorticoid or aspirin inhibit the activation of NF-κB and/or repress the production of NO or prostaglandin as an important anti-inflammatory mechanism of them. Moreover, herbal drugs widely used as an anti-inflammatory agent in oriental folk medicine are known to exert their effects by the inhibition of NF-κB activity (E. Kopp, S. Ghosh, *Science*, 1994, 265, 956–959; A. Ray, K. E. Prefontaine, *Proc. Natl. Acad. Sci. U.S.A.*, 1994, 91, 752–756). Thus, NF-κB plays not only a central role in the expression of inflammatory mediators in immune cells and neuronal cell death but also an important role in the regulation of the expression of proteins which inhibit the apoptosis of cancer cells induced by TNF-α or anti-cancer agents.

Meanwhile, current status on the development of inhibitors of NO, NF-κB, and TNF-α is described below:

Inhibitors of NO production have focused on the development of agents that specifically inhibit the enzymatic activities of iNOS. For example, analogues of NO precursor such as L-arginine and L-citrulline and derivatives of aminoguanidine and isothiourea are under active investigation (Babu, B. R. B., Griffith O. W., *Current Opinion in Chemical Biology*, 1998, 2, 491–500).

Curcumin, capsacin, caffeic acid derivative, tetrandrine, and sanguinarine have been reported to inhibit the activation of NF-κB, and dexamethasone, a representative anti-inflammatory agent of glucocorticoid, inhibit NO production by inhibiting the expression of iNOS gene. The molecular mechanism of dexamethasone in the NO synthesis has been known to be the inhibition of NF-κB activation by induction of I-κB, resulting the suppression of iNOS gene transcription (De Vera, M. E. et al., *Am. J. Physiol.*, 1997, 273, 1290–1296).

There are several drugs, which show inhibitory activity for TNF-α production, including IL-4, IL-10 and tumor growth factor-β (TGF-β), and clinical trials using antibody against TNF-α and soluble TNF-α receptor are underway. As synthetic compounds, pentoxifylline, thaliodomide, and SKF 86002, which is a member of bicyclic imidazole, have been developed. Nevertheless, there has yet to be developed any compound to inhibit TNF-α production for the purpose of a therapeutic agent (A. Eigler et al., *Immunology Today*, 1997, 18, 487–492).

Meanwhile, about 200 diterpene compounds have been reported from *Isodon japonicus* or close relatives thereof until now. However, there has been no report indicating not only that these compounds inhibit the production of NO, $PGE_2$, or TNF in cell lines stimulated by LPS but also that these compounds inhibit the activation of NF-κB.

Therefore, the present inventors have designed the present invention to show that kamebanin, kamebacetal A, kamebakurin, and exisanin A, each of which is a member of the kaurane diterpene compound isolated from the methanol extract of *Isodon japonicus*, inhibit not only the activation of NF-κB, but also the production of NO, prostaglandin, and TNF-α in the LPS-stimulated macrophage cells. These four compounds are useful as therapeutic agents for the treatment of inflammatory diseases, immunological diseases, and cancer.

SUMMARY OF THE INVENTION

The object of the present invention is to provide diterpene compounds having significant anti-inflammatory or anti-cancer activity, which is useful not only as a therapeutic agent against inflammatory diseases, immunological diseases, but also as an auxiliary agent in the chemotherapy or radiation therapy for cancer.

BRIEF DESCRIPTION OF THE DRAWINGS

1) the inhibition of Bfl-1/A1 mRNA expression at the MCF-7 cell line 2) the inhibition of Bfl-1/A1 mRNA expression at the HT1080 cell line

DETAILED DESCRIPTION OF PREFERRED EMBODIMENTS

A terminology and technology referred in the present detailed description are used as general meaning of the technical field, which includes the present invention. In addition, references mentioned in the present detailed description are all included in the present detailed description for describing the present invention.

The present invention provides kamebanin, kamebacetal A, kamebakaurin, and exisanin A, each of which is a member of kaurane diterpene compounds, having remarkable anti-inflammatory and anti-cancer activity.

In addition, the present invention provides pharmaceutical compositions for the treatment and prevention of inflammatory disease, immunological disease, and cancer, comprising the compounds as an active ingredient, showing less toxicity and remarkable effect.

In addition, the present invention provides the use of the compounds for the treatment and prevention of inflammatory disease, immunological disease, and cancer.

Hereinafter, the present invention is described in detail.

The present invention provides kamebanin represented by Chemical Formula 1, kamebacetal A represented by Chemical Formula 2, kamebakaurin represented by Chemical Formula 3, and exisanin A represented by Chemical Formula 4, each of which is a member of kaurane diterpene compounds <Chemical formula 1>

<Chemical formula 2>

<Chemical formula 3>

<Chemical formula 4>

The present inventors isolated kamebanin, kamebacetal A, kamebakaurin, and exisanin A, each of which is a member of the kaurane diterpene compounds from the methanol extract of *Isodon japonicus*.

The method of isolating kaurane diterpene compounds of the present invention comprises the following steps:

(1) extracting *Isodon japonicus* using organic solvent;
(2) re-extracting the resulting extract of step 1 using organic solvent; and
(3) purifying the resulting extract of step 2 by repeated column chromatography.

In step 1, *Isodon japonicus* was extracted three times using organic solvent, and the extract was obtained by concentrating the resultant. In a preferred embodiment of the present invention, methanol extract was obtained using methanol as an organic solvent.

In step 2, re-extract was obtained by fractionation of the extract from step 1 using organic solvent and water. Dichloromethane is preferred organic solvent in this step.

In step 3, the extract of step 2 was dissolved in methanol and washed with n-hexane. The resulting extract was loaded on the first silica gel column chromatography and six fractions were obtained by eluting with dichloromethane-methanol step gradient system.

Among six fractions, the second fraction was loaded on the second column chromatography, and four fractions, 2-A, 2-B, 2-C, and 2-D, were obtained by elution with hexane-acetone step gradient system. Kamebanin represented by Chemical Formula 1 was obtained by applying fraction 2-B to the Sephadex LH-20 column.

The third fraction obtained by the first silica gel column chromatography was loaded on the third silica gel column chromatography, and four fractions, 3-A, 3-B, 3-C and 3-D, were obtained by elution with hexane-ethylacetate step gradient system. Kamebacetal A represented by Chemical Formula 2 was isolated from the 3-B fraction, and kamebakaurin represented by Chemical Formula 3 was isolated from the 3-C fraction.

The fourth fraction obtained by the first silica gel column chromatography was loaded on the fourth silica gel column chromatography. Exisanin A represented by Chemical Formula 4 was isolated by elution with n-hexane-acetone step gradient system.

The yield of the diterpene compounds isolated by above method was 15 mg of kamebanin, 62 mg of kamebacetal A, 210 mg of kamebakaurin, and 135 mg of exisanin A, indicating that kamebakaurin is the most abundant.

In addition, the present invention provides pharmaceutical compositions for the treatment and prevention of inflammatory disease, immunological disease, and cancer, comprising the compounds as an active ingredient, showing less toxicity and significant effect.

Kaurane diterpene compounds of the present invention can be administered orally or parenterally and can be used in general forms of pharmaceutical formulation.

The compounds of the present can be prepared for oral or parenteral administration by mixing with generally-used fillers, extenders, binders, wetting agents, disintegrating agents, diluents such as surfactant, or excipients.

The present invention also includes pharmaceutical formulations in dosage units. This means that the formulations are present in the form of individual parts, for example, tablets, coated tablets, capsules, pills, suppositories, and ampules, the active compound content of which corresponds to a fraction or a multiple of an individual dose. The dosage units can contain, for example, one, two, three, or four individual doses or ½, ⅓, or ¼ of an individual dose. An individual dose preferably contains the amount of active compound, which is administered in one application and which usually corresponds to one whole, one half, one third, or one quarter of a daily dose.

Non-toxic inert pharmaceutically suitable excipients are to be understood as solid, semi-solid, or liquid diluents, fillers, and formulation auxiliaries of all types.

Preferred pharmaceutical formulations which, may be mentioned are tablets, coated tablets, capsules, pills, granules, suppositories, solutions, suspensions and emulsions, pastes, ointments, gels, creams, lotions, dusting powders, and sprays.

Solid formulations for oral administration are tablets, pills, dusting powders, and capsules, while liquid formulation for oral administrations are suspensions, solutions, emulsions, and syrups. These formulations can contain various excipients such as wetting agents, sweeteners, aromatics, and preservatives in addition to generally used simple diluents such as water and liquid paraffin.

Tablets, coated tablets, capsules, pills, and granules can contain the active compound or compounds in addition to the customary excipients. Examples of such excipients include fillers and extenders (e.g., starches, lactose, sucrose, glucose, mannitol, and silicic acid), binders (e.g., carboxymethylcellulose, alginates, gelatine, and polyvinylpyrrolidone), humectants (e.g., glycerol), disintegrating agents (e.g., agar-agar, calcium carbonate, and sodium carbonate), solution retarders (e.g., paraffin), absorption accelerators (e.g., quaternary ammonium compounds), wetting agents (e.g., cetyl alcohol and glycerol monostearate), adsorbents (e.g., kaolin and bentonite), lubricants (e.g., talc, calcium stearate, magnesium stearate, and solid polyethylene glycols), and mixtures of any of the these substances.

The tablets, coated tablets, capsules, pills, and granules can be provided with the customary coatings and shells, optionally containing opacifying agents, and can also be of a composition such that they release the active compound or compounds only or preferentially in a certain part of the intestinal tract. If appropriate in a delayed manner, examples of embedding compositions are polymeric substances and waxes.

If appropriate, the active compound or compounds can also be present in microencapsulated form with one or more of the above-mentioned excipients.

Formulations for parenteral administration are sterilized aqueous solutions, water-insoluble excipients, suspensions, emulsions, and suppositories.

Suppositories can contain, in addition to the active compound or compounds, the customary water-soluble or water-insoluble excipients (e.g., polyethylene glycols), fats (e.g., cacao fat), higher esters (e.g., C14-alcohol with C16-fatty acid), or mixtures of these substances.

Ointments, pastes, creams, and gels can contain, in addition to the active compound or compounds, the customary excipients, for example, animal and vegetable fats, waxes, paraffins, starch, tragacanth, cellulose derivatives, polyethylene glycols, silicones, bentonites, silicic acid, talc, and zinc oxide, or mixtures of these substances.

Dusting powders and sprays can contain, in addition to the active compound or compounds, the customary excipients, for example, lactose, talc, silicic acid, aluminum hydroxide, calcium silicate, and polyamide powder, or mixtures of these substances. Sprays can additionally contain the customary propellants, for example, chlorofluorohydrocarbons.

Solutions and emulsions can contain, in addition to the active compound or compounds, the customary excipients. Examples of these excipients include solvents, solubilizing agents, and emulsifiers (e.g., water, ethyl alcohol, isopropyl alcohol, ethylcarbonate, ethyl acetate, benzyl alcohol, benzyl benzoate, propylene glycol, 1,3-butylene glycol, dimethylformamide, oils and in particular cottonseed oil, groundnut oil, corn germ oil, olive oil, castor oil, and sesame oil), glycerol, glycerol formal, tetrahydrofurfuyl alcohol, polyethylene glycols, and fatty acid esters of sorbitan, or mixtures of these substances.

For parenteral administration, the solutions and emulsions are also in a sterile form, which is isotonic with blood.

Suspensions can contain, in addition to the active compound or compounds, the customary excipients, such as liquid diluents (e.g., water, ethyl alcohol, and propylene glycol) and suspending agents (e.g., ethoxylated isostearyl alcohols, polyoxyethylene sorbitol, and sorbitan esters), microcrystalline cellulose, aluminum metahydroxide, bentonite, agar-agar, and tragacanth, or mixtures of these substances.

The formulation forms mentioned can also contain coloring agents, preservatives, additives which improve the smell and taste (e.g., peppermint oil and eucalyptus oil), and sweeteners (e.g., saccharin).

The above-mentioned pharmaceutical formulations can also contain other pharmaceutical active compounds in addition to the compounds according to the present invention.

The above-mentioned pharmaceutical formulations are prepared in the customary manner by known methods, for example, by mixing the active compound or compounds with the excipient or excipients.

The therapeutically active compounds should preferably be present in the above-mentioned pharmaceutical formulations in a concentration of about 0.1 to 99.5% by weight of the total mixture, preferably about 0.5 to 95% by weight of the total mixture.

The formulations mentioned can be used on humans and animals, either orally, rectally, parenterally (intravenously, intramuscularly, or subcutaneously), intracisternally, intravaginally, intraperitoneally, or locally (i.e., dusting powder, ointment, or drops), and for the therapy of infections in hollow spaces of the body and in body cavities. Possible suitable formulations are injection solutions. Solutions and suspensions for oral therapy and gels, infusion formulations, emulsions, ointments or drops, ophthalmological and dermatological formulations, silver salts and other salts, ear drops, eye ointments, dusting powders or solutions can be used for local therapy. In the case of animals, intake can also be in suitable formulations via the feed or drinking water. Gels, powders, dusting powders, tablets, delayed release tablets, premixes, concentrates, granules, pellets, boli, capsules, aerosols, sprays, and inhalants can furthermore be used on humans and animals. The compounds according to the present invention can moreover be incorporated into other carrier materials, such as plastics (chain of plastic for local therapy), collagen, or bone cement.

Effective dosage of each of the kaurane diterpene compounds of the present invention is described below.

In the case of kamebakaurin, an effective dosage is in the range of 10 to 500 mg/kg, more preferably 50–250 mg/kg; in the case of kamenanin, an effective dosage is in the range of 10 to 500 mg/kg, more preferably 50–250 mg/kg; in the case of kamebacetal A, an effective dosage is in the range of 10 to 500 mg/kg, more preferably 50–250 mg/kg; and in the case of exisanin A, an effective dosage is in the range of 10 to 500 mg/kg, more preferably 50–250 mg/kg. Each compound can be administered one to three times per day, if appropriate in the form of several individual doses, to achieve the desired results. However, it may be necessary to deviate from the dosages mentioned, and in particular, to do so as a function of the nature and body weight of the subject to be treated, the nature and severity of the disease, the nature of the formulation of the administration of the medicament, and the period or interval within which administration takes place.

Thus, in some cases, less than the above-mentioned amounts of active compound will suffice, while in other cases, the above-mentioned amounts must be exceeded. The particular optimum dosage and mode of administration required for the active compounds can be determined by any expert in the field.

In addition, the present invention provides the use of the compounds for the treatment and prevention of inflammatory disease, immunological disease, and cancer.

To investigate the efficacy of kaurane diterpene compounds of the present invention for the therapeutic agent of inflammatory disease, immunological disease, and cancer, the four kinds of compound were applied to macrophage cell lines stimulated by LPS. After that, the effect of each compound on the activation of transcription factor NF-κB, which regulates the production and the expression of inflammatory agents, such as NO, prostaglandin E2, and TNF-α, was studied. As a result, NO synthesis by LPS was inhibited dose-dependently by the treatment of kaurane diterpene compounds of the present invention (see Table 1). In addition, the effect of kaurane diterpene compounds of the present invention on the production of prostaglandin E2 was investigated using enzyme immunometric assay. As a result, prostaglandin E2 production was inhibited dose-dependently by the treatment of kaurane diterpene compounds of the present invention, too (see Table 2).

When the effect of kaurane diterpene compounds of the present invention on the production of TNF-α, one of the inflammatory mediators, which exhibits cytotoxic effect and induces the production of prostaglandin and cytokines, was investigated using enzyme immunometric assay, it was found that TNF-α production was inhibited dose-dependently by the treatment of kaurane diterpene compounds of the present invention (see Table 3).

When kaurane diterpene compounds of the present invention were investigated for their effect on the activation of transcription factor NF-κB, which regulates the expression of iNOS and cyclooxygenase, and TNF-α, it was found that the activity of SEAP representing in turn the activity of NF-κB induced by LPS was inhibited dose-dependently by the treatment of kaurane diterpene compounds of the present invention (see Table 4). To confirm these results, when the effect of kaurane diterpene compounds on the DNA binding activity of NF-κB was investigated by gel-shift assay, it was found that DNA binding activity of NF-κB induced by LPS was inhibited dose-dependently by kaurane diterpene compounds of the present invention (see FIG. 1).

To study the possibility of the kaurane diterpene compounds as a therapeutic agent, acute toxicity test was performed using six-week-old specific-pathogen free (SPF) SD-line rats. As a result, the tested compounds did not show any toxic effect. Therefore, the compounds used in this experiment are evaluated to be safe substances, having $LD_{50}$ values at least more than 0.5 g/kg in rats.

From these results, it is obvious that four kinds of kaurane diterpene compounds of the present invention are useful as a therapeutic agent for the treatment of inflammatory diseases, immunological diseases, and cancer.

To suggest the use of the kaurane diterpene compounds as therapeutic agents for inflammatory diseases and immunological diseases, or as an auxiliary agent in the chemotherapy and radiation therapy for cancer, the following experiment was performed using kamebakaurin.

Figure 2A:
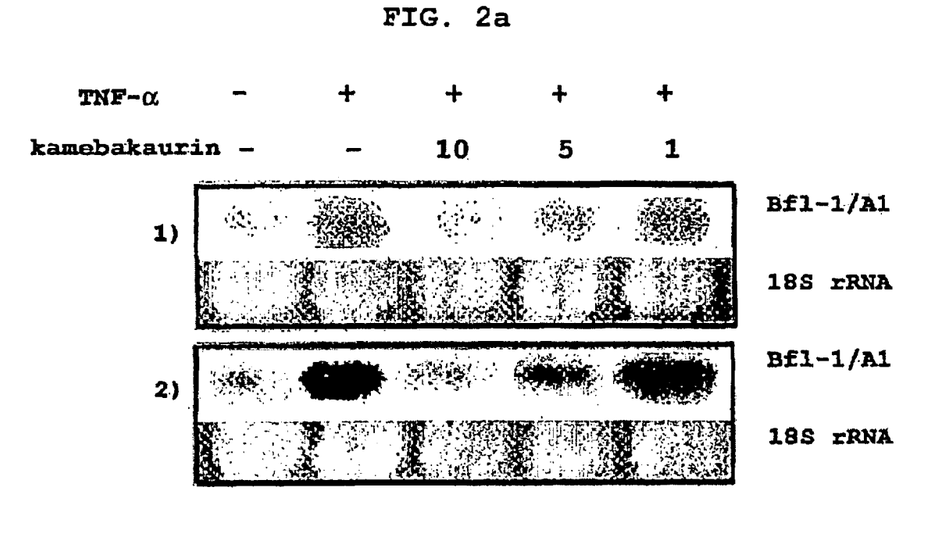
FIG. 2a shows the result of Northern blot analysis showing inhibition of mRNA expression of antiapoptotic protein Bfl-1/A1 by kamebakaurin, one of the kaurane diterpene compound of the present invention.
Figure 2B:
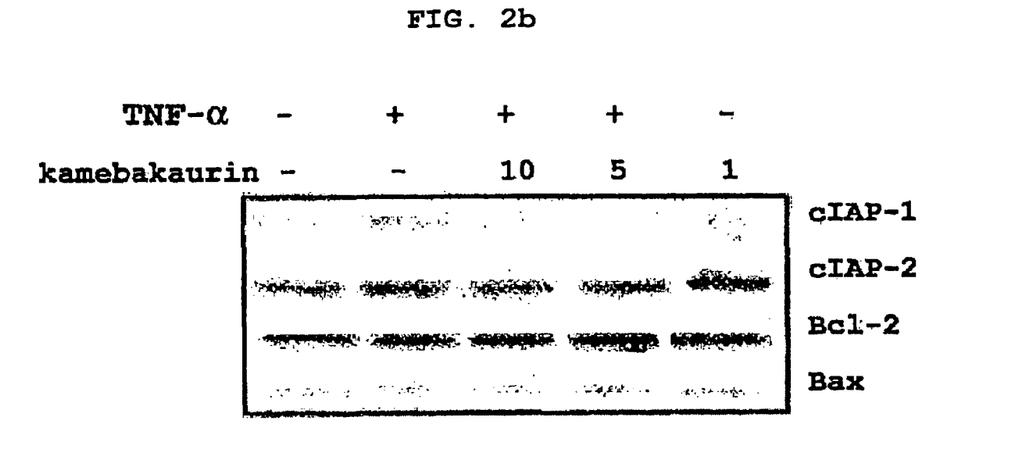
FIG. 2b shows the result of Western blot analysis that mRNA expression of antiapoptotic proteins cIAP-1 and cIAP-2, which are regulated by NF-κB, is inhibited by kamebakaurin, one of the kaurane diterpene compound of the present invention, whereas mRNA expression of Bcl-2 and Bax genes, which are not regulated by NF-κB, is not inhibited by kamebakaurin.

When the effect of kaurane diterpene compounds on the production of inflammatory mediators, such as NO and prostaglandin, and on the expression of iNOS and COX-2 were investigated by RT-PCT and Western blot analysis, it was found that the expression of iNOS and COX mRNA was inhibited by 1 μg/ml of kamebakaurin (see FIG. 2a), and the expression of iNOS and COX-2 proteins was inhibited dose-dependently by kamebakaurin (see FIG. 2b).

In addition, when anti-inflammatory effect of kamebakaurin was tested in the adjuvant arthritis animal model by the method of N. Futaki et al., (General Pharmacology, 1993, 24, 105–110), it was found that arthritis was suppressed dose-dependently by kamebakaurin.

Figure 3A:
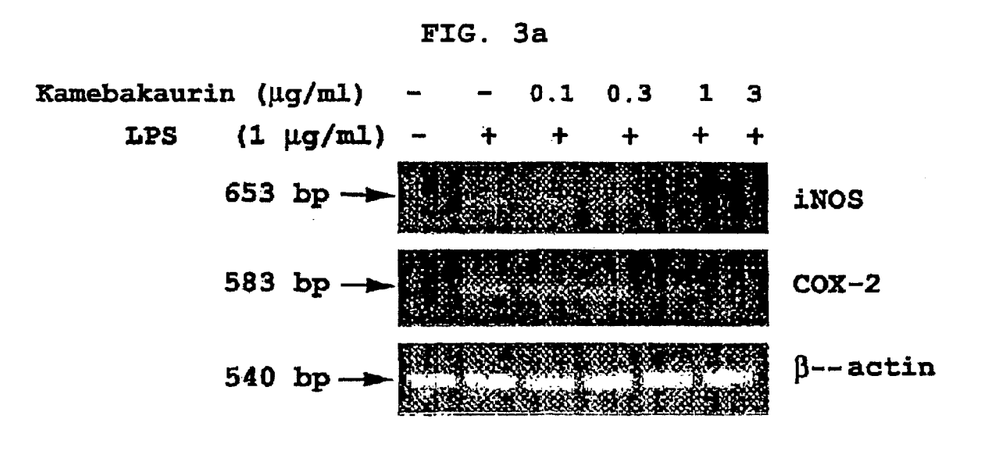
FIG. 3a shows the result of RT-PCT (reverse transcription polymerase chain reaction) showing the inhibition of MRNA expressions of iNOS (inducible nitric oxide synthetase) and COX-2 (cyclooxygenase-2) by kamebakaurin, one of the kaurane diterpene compound of the present invention.

When the effect of kamebakaurin on the expression of anti-apoptotic genes, such as Bfl-1/A1, cIAP-1, and cIAP-2, was investigated by Northern or Western blot analysis, it was found that the expression of Bfl-1/A1 was inhibited by kamebakaurin (see FIG. 3a). In addition, when the effect of kamebakaurin on the expression of cIAP-1 and cIAP-2 proteins was investigated by Western blot analysis, it was found that the expression of cIAP-1 and cIAP-2 proteins was inhibited by kamebakaurin (see FIG. 3b).

Figure 4:
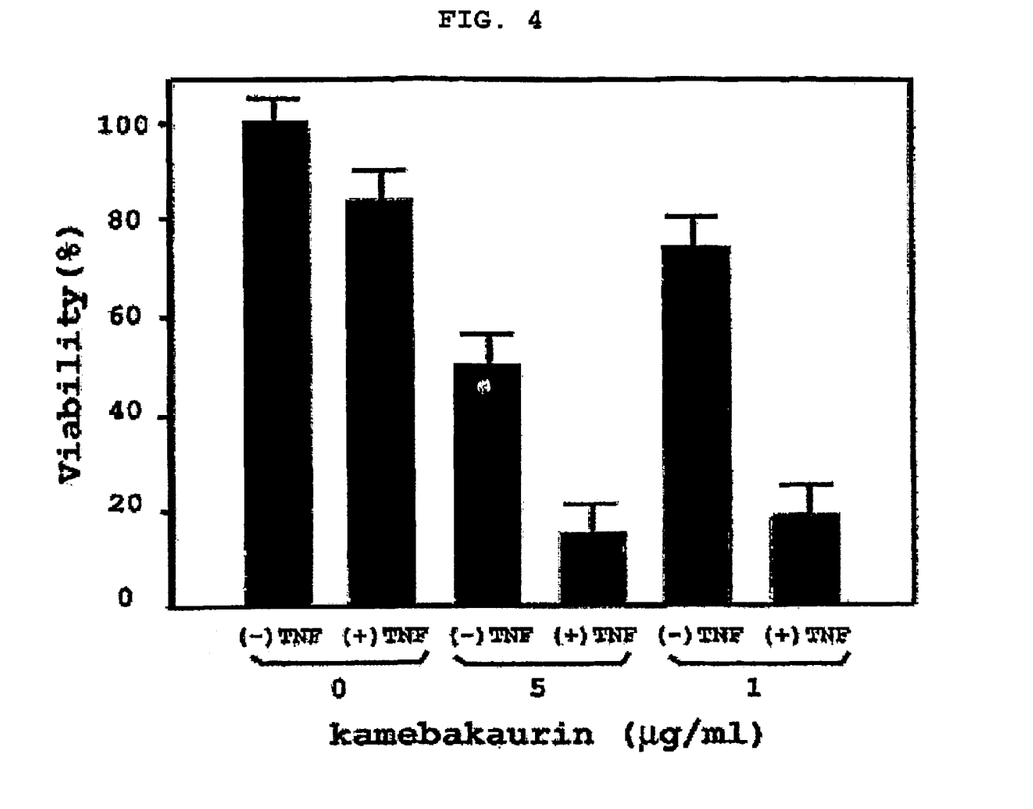
FIG. 4 shows the result of measuring the potentiation of TNF-α-induced cytotoxicity by kamebakaurin, one of the kaurane diterpene compound of the present invention.

Moreover, when the effect of kamebakaurin on the cytotoxic activity of TNF-α was investigated by MTT assay, it was found that the cytotoxic activity of TNF-α was increased by kamebakaurin (see FIG. 4).

From these results, it is obvious that kamebakaurin of the present invention can be used not only as a therapeutic agent for the treatment of inflammatory diseases and immunological diseases, but also as an anti-cancer agent.

Particularly, kamebakaurin have characteristics of not only inhibiting over-production of NO, prostaglandin, and TNF but also inhibiting the activation of NF-κB, which plays an important role in the expression of inflammatory cytokines, adhesion molecules, and anti-apoptotic proteins, thereby can be used as a therapeutic agent for the treatment of inflammatory diseases and immunological diseases. Here, the inflammatory diseases and immunological diseases may be arthritis, septic shock, autoimmune diseases, or diseases related to the death of neuron cells. Moreover, kamebakaurin can be used as an anti-cancer agent, by its characteristics of inhibiting the expression of anti-apoptotic proteins, which are encoded by NF-κB target genes.

EXAMPLES

Practical and currently preferred embodiments of the present invention are illustrative as shown in the following Examples.

However, it will be appreciated that those skilled in the art, on consideration of this disclosure, may make modifications and improvements within the spirit and scope of the present invention.

Example 1

Isolation of Kaurane Diterpene Compounds

After extracting 4.3 kg of dried *Isodon japonicus* with methanol three times and concentrating the resultant, 203 g of methanol extract was obtained and partitioned using dichloromethane and water.

After obtaining 84.6 g of dichloromethane extract and dissolving the extract in 90% methanol, the extract was washed three times with n-hexane. After loading 18 g of concentrated 90% methanol solution to the first silica gel column chromatography followed by elution with a dichloromethane-methanol step gradient system, six fractions were obtained.

After loading 2 g of the second fraction obtained by the first gel column chromatography on the second silica gel column chromatography, the column was eluted with hexane-acetone step gradient system of 5:1, 3:1, 3:2, and 0:1 ratio, to obtain four fractions, 2-A, 2-B, 2-C, and 2-D.

Among the fractions. of the second silica gel column chromatography, fraction 2-B was subjected to a Sephadex LH-20 column chromatography, and 15 mg of kamebanin represented by Chemical Formula 1 was obtained.

In addition, after loading 3 g of the third fraction obtained by the first gel column chromatography on the third silica gel column chromatography followed by elution with hexane-ethylacetate step gradient system, four fractions, 3-A, 3-B, 3-C, and 3-D, were obtained. From 3-B fraction, 62 mg of kamebacetal A represented by Chemical Formula 2 was obtained, and from 3-C fraction, 210 mg of kamebakaurin represented by Chemical Formula 3 was obtained.

In addition, after loading the fourth fraction obtained by the first silica gel column chromatography on the fourth silica gel column chromatography followed by elution with hexane-acetone step gradient system, 135 mg of exisanin A represented by Chemical Formula 4 was obtained.

The yield of the diterpene compounds isolated by above method was 15 mg of kamebanin, 62 mg of kamebacetal A, 210 mg of kamebakaurin, and 135 mg of exisanin A, showing that kamebakaurin is the most abundant.

Example 2

Inhibitory Effect of Kaurane Diterpene Compound on the Production of NO

To investigate whether kaurane diterpene compounds obtained in Example 1 can inhibit the production of nitric oxide (NO) which induces apoptosis of the immune and neuron cells, the present inventors measured the amount of nitrite ($NO_2$) accumulated in the culture medium of LPS-stimulated murine macrophage cells, which were treated with four kaurane diterpene compounds, kamebanin, kamebacetal A, kamebakaurin, or exisanin A.

In detail, Raw 264.7 murine macrophage cells (ATCC TIB-71) in DMEM medium were seeded to 96-well plate at a cell density of $1 \times 10^5$ cells/well and incubated for 3 hours at 37° C., 5% $CO_2$ incubator. To induce NO synthesis in the macrophage cell, 1 μg/ml of LPS and 3 μg/ml, 0.3 μg/ml, and 0.03 μg/ml of kaurane diterpene compounds of the present invention were added to the medium and the plate was incubated for 24 hours. The amount of $NO_2$, the final oxidation product of NO induced by the LPS in the medium was measured as followed. After collecting and centrifuging incubated medium, 100 μl of Griess reagent was added into 100 μl of each culture medium. Then, the medium was incubated for ten minutes at room temperature and absorbance at 550 nm wavelength was measured. Griess reagent was prepared by mixing a solution, wherein 1% sulfanilamide was dissolved in 5% phosphoric acid, and a solution of 0.1% naphyhylethylenediamine-HCl by a 1:1 ratio. To measure the amount of standard NO synthesis, $NaNO_2$ was serially diluted and the absorbance was measured after reacting it with Griess reagent. From this, the standard curve for the amount of NO production was obtained. The amount of NO production in the culture medium treated with each compound was estimated using standard curve for NO determination. Table 1 shows the result.

TABLE 1

Inhibitory effect of kaurane diterpene compounds on the production of NO

| Sample | Conc. (μg/ml) | NO (μM) | Inhibition rate (%) | $IC_{50}$ (μM) |
| --- | --- | --- | --- | --- |
| (−) LPS | | 3.3 ± 0.3 | 100.0 | |
| (+) LPS | | 49.6 ± 1.8 | 0.0 | |
| Kamebanin | 3 | 3.6 ± 0.3 | 99.3 | 0.06 |
| | 0.3 | 4.6 ± 0.6 | 97.2 | |
| | 0.03 | 23.4 ± 1.3 | 56.5 | |
| Kamebacetal A | 3 | 3.3 ± 0.7 | 100.0 | 0.58 |
| | 0.3 | 19.9 ± 3.7 | 64.2 | |
| | 0.03 | 38.5 ± 4.8 | 23.9 | |
| Kamebakaurin | 3 | 3.6 ± 0.7 | 99.3 | 0.15 |
| | 0.3 | 16.1 ± 2.8 | 72.4 | |
| | 0.03 | 29.1 ± 4.2 | 44.2 | |
| Exisanin A | 3 | 6.7 ± 0.8 | 92.5 | 0.35 |
| | 0.3 | 22.2 ± 2.3 | 59.3 | |
| | 0.03 | 32.5 ± 3.5 | 37.0 | |

As is shown in Table 1, NO production by LPS was inhibited dose-dependently by the treatment of kaurane diterpene compounds of the present invention. $IC_{50}$ for the NO production was 0.06 μM, 0.584 μM, 0.15 μM, and 0.35 μM in the case of kamebanin, kamebacetal A, kamebakaurin, and exisanin A, respectively, indicating potent inhibition of NO production by these compounds. Especially, when 3 μg/ml concentrations of kamebacetal A was added, No production was nearly the same as that of the negative control in which LPS was not treated at all.

Example 3

Inhibitory Effect of Kaurane Diterpene Compounds on the Production of Prostaglandin $E_2$ To investigate whether kaurane diterpene compounds obtained in Example 1 can inhibit the production of prostaglandin, which induces inflammatory reaction, the present inventors measured the amount of prostaglandin E2 accumulated in the culture medium of LPS-stimulated murine macrophage cells, which were treated with four kaurane diterpene compounds, kamebanin, kamebacetal A, kamebakaurin, or exisanin A.

In detail, Raw 264.7 cells in DMEM medium were seeded to a 96-well plate at a cell density of $1 \times 10^5$ cells/well and were incubated for 18 hours. Cyclooxygenase-1, the constitutive rate-determining enzyme of the prostaglandin synthesis was inactivated by incubating for 3 hrs with 500 μM of aspirin and each well was washed two times with PBS (phosphate-buffered saline). To each well were added 1 μg/ml of LPS and 3 μg/ml, 0.3 μg/ml, and 0.03 μg/ml concentrations of kaurane diterpene compounds of the present invention and was incubated for 16 hours. After collecting supernatant by centrifugation, the amount of prostaglandin in the culture medium was quantified by enzyme immunometric assay. Table 2 shows the result.

TABLE 2

Inhibitory effect of kaurane diterpene compounds on the production of prostaglandin E2

| Sample | Conc. (μg/ml) | $PGE_2$ (ng/ml) | Inhibition rate (%) | $IC_{50}$ (μM) |
| --- | --- | --- | --- | --- |
| (−) LPS | | 1.1 ± 0.5 | 100.0 | |
| (+) LPS | | 11.9 ± 1.4 | 0.0 | |
| Kamebanin | 3 | 0.7 ± 0.1 | 104.2 | 0.88 |
| | 0.3 | 4.0 ± 0.3 | 73.9 | |
| | 0.03 | 14.4 ± 2.2 | −22.5 | |
| Kamebacetal A | 3 | 2.7 ± 0.4 | 85.6 | 2.80 |
| | 0.3 | 9.8 ± 1.4 | 19.6 | |
| | 0.03 | 13.2 ± 0.8 | −11.3 | |
| Kamebakaurin | 3 | 1.8 ± 0.4 | 95.1 | 2.63 |
| | 0.3 | 9.2 ± 0.2 | 9.7 | |
| | 0.03 | 10.7 ± 1.2 | −7.1 | |
| Exisanin A | 3 | 5.7 ± 0.7 | 57.7 | 5.37 |
| | 0.3 | 10.7 ± 1.3 | 11.7 | |
| | 0.03 | 13.7 ± 0.3 | −16.1 | |

As is shown in Table 2, prostaglandin E2 production was inhibited dose-dependently by the treatment of kaurane diterpene compounds of the present invention. $IC_{50}$ was 0.88 μM, 2.80 μM, 2.63 μM, and 5.37 μM in the case of kamebanin, kamebacetal A, kamebakaurin, and exisanin A, respectively, indicating potent inhibition of prostaglandin E2 production by these compounds. The treatment of 3 μg/ml concentrations of kamebakaurin resulted in the decrease of up to 95% of the prostaglandin E2 synthesis. Especially, when 3 μg/ml concentrations of kamebanin was added, prostaglandin production was nearly the same as that of the negative control in which LPS was not treated at all.

Example 4

Inhibitory Effect of Kaurane Diterpene Compounds on the Production of TNF-α

To investigate whether kaurane diterpene compounds obtained in Example 1 can inhibit effectively the production of tumor necrosis factor-α (TNF-α), one of the inflammatory mediator, which confers cytotoxic effect and induces the production of prostaglandin and cytokines, the present inventors measured the amount of TNF-α accumulated in the culture medium of LPS-stimulated murine macrophage cells, which were treated with four kaurane diterpene compounds, kamebanin, kamebacetal A, kamebakaurin, or exisanin A.

In detail, Raw 264.7 cells in DMEM medium were seeded to a 96-well plate at a cell density of $1\times10^5$ cells/well and were incubated for 3 hours at 37° C. in a 5% $CO_2$ incubator. To each well were added 1 μg/ml of LPS and 3 μg/ml, 0.3 μg/ml, and 0.03 μg/ml concentrations of kaurane diterpene compounds of the present invention and was incubated for 16 hours. After collecting supernatant by centrifugation, the amount of TNF-α in the culture medium was quantified by enzyme immunometric assay. Table 3 shows the result.

TABLE 3

Inhibitory effect of kaurane diterpene compounds on the production of TNF-α

| Sample | Conc. (μg/ml) | TNF-α (pg/ml) | Inhibition rate (%) | $IC_{50}$ (μM) |
|---|---|---|---|---|
| (−) LPS | | 17.1 ± 1.0 | 100.0 | |
| (+) LPS | | 1669.0 ± 129.0 | 0.0 | |
| Kamebanin | 3 | 19.8 ± 0.7 | 99.8 | 1.00 |
| | 0.3 | 805.6 ± 195.4 | 52.3 | |
| | 0.03 | 1835.0 ± 158.8 | −10.0 | |
| Kamebacetal A | 3 | 38.9 ± 1.0 | 98.7 | 0.60 |
| | 0.3 | 691.4 ± 152.7 | 59.2 | |
| | 0.03 | 1495.0 ± 239.7 | 10.5 | |
| Kamebakaurin | 3 | 29.6 ± 5.3 | 99.2 | 0.53 |
| | 0.3 | 654.4 ± 29.4 | 61.3 | |
| | 0.03 | 1407.0 ± 255.6 | 15.9 | |
| Exisanin A | 3 | 103.2 ± 12.8 | 94.8 | 0.61 |
| | 0.3 | 936.1 ± 0.00 | 44.4 | |
| | 0.03 | 1243.0 ± 195.6 | 25.8 | |

As is shown in Table 3, TNF-α production was inhibited dose-dependently by the treatment of kaurane diterpene compounds of the present invention. $IC_{50}$ was 1.0 μM, 0.60 μM, 0.53 μM, and 0.61 μM in the case of kamebanin, kamebacetal A, kamebakaurin, and exisanin A, respectively, indicating potent. inhibition of TNF-α production by these compounds. The treatment of 3 μg/ml concentrations of all diterpene compounds resulted in the decrease of up to 90% of TNF-α production.

From the results of Example 1 to Example 4, the present inventors found that kaurane diterpene compounds isolated from *Isodon japonicus* inhibited effectively the production of NO, which induces immunological disorders and apoptosis of neuron cells, as well as the production of prostaglandin and TNF-α, which are inflammatory mediator, ensuring that these compounds could be useful as therapeutic agents for inflammatory diseases and immunological diseases.

Example 5

Inhibitory Effect of Kaurane Diterpene Compounds on the Activation of NF-κB

To investigate whether kaurane diterpene compounds obtained in Example 1 can inhibit the activity of transcription factor NF-κB, which regulates the expression of iNOS and cyclooxygenase, which are essential for the production of NO, and prostaglandin, respectively, and TNF-α, the present inventors performed the following experiments.

<5-1> Inhibitory Effect of Kaurane Diterpene Compounds on the Activation of NF-κB RAW-NF-AP cells, which can be used effectively to detect the NF-κB dependent expression of reporter gene, (Korean Patent Application No. 1999-0006025), were seeded to a 96-well plate at a cell density of $1\times10^5$ cell/well and were incubated for 3 hours at 37° C. in a 5% $CO_2$ incubator. Thereafter, 1 μg/ml concentration of LPS and 0.03 μg/ml, 0.3 μg/ml, and 3 μg/ml concentrations of kaurane diterpene compounds of the present invention were added to each well and was incubated for 16 hours. After collecting supernatant by centrifugation, the amount of secreted alkaline phosphatase (SEAP) in the culture medium of which expression is regulated by the activation of NF-κB was quantified. Table 4 shows the result.

TABLE 4

Inhibitory effect of kaurane diterpene compounds on the activation of NF-κB

| Sample | Conc. (μg/ml) | Inhibition of SEAP activity (%) | $IC_{50}$ (μM) |
|---|---|---|---|
| (−) LPS | | 100.0 | |
| (+) LPS | | 0.0 | |
| Kamebanin | 3 | 99.7 | 0.72 |
| | 0.3 | 48.5 | |
| | 0.03 | 0.6 | |
| Kamebacetal A | 3 | 110.4 | 2.45 |
| | 0.3 | 62.2 | |
| | 0.03 | 1.3 | |
| Kamebakaurin | 3 | 96.4 | 1.11 |
| | 0.3 | 33.1 | |
| | 0.03 | 2.5 | |
| Exisanin A | 3 | 93.7 | 1.66 |
| | 0.3 | 19.4 | |
| | 0.03 | −2.6 | |

As is shown in Table 4, the activity of SEAP showing in turn the activity of NF-κB induced by LPS was inhibited dose-dependently by the treatment of kaurane diterpene compounds of the present invention. The treatment of 3 μg/ml concentrations of all of the four diterpene compounds resulted in the decrease of up to 90% of SEAP activity. Especially, kamebacetal A inhibited SEAP activity to the extent of negative control in which LPS was not treated at all.

<5-2> Inhibitory Effect of Kaurane Diterpene Compounds on the DNA Binding Activity of NF-κB Finding the inhibitory effect of kaurane diterpene compounds on the NF-κB activation in Example <5-1>, the present inventors investigated the effect of kaurane diterpene compound on the DNA binding activity of NF-κB by the following experiment.

In detail, after pretreatment of Raw 264.7 murine macrophage cells with 0 μg/ml, 1 μg/ml, 5 μg/ml, and 10 μg/ml concentrations of kaurane diterpene compounds of the present invention for thirty minutes, Raw 264.7 cells were stimulated with 1 μg/ml concentrations of LPS. After incubating 20 μg of nucleus extract prepared from above macrophage cells with radio-labeled double strand oligonucleotide represented by SEQ. ID NO. 1 for 30 minutes, the incubation mixture were subjected to non-denaturing polyacrylamide gel electrophoresis. Protein-DNA complex was transferred to Whattman 3 MM cellulose membrane and then the membrane was exposed to x-ray film.

Figure 1:
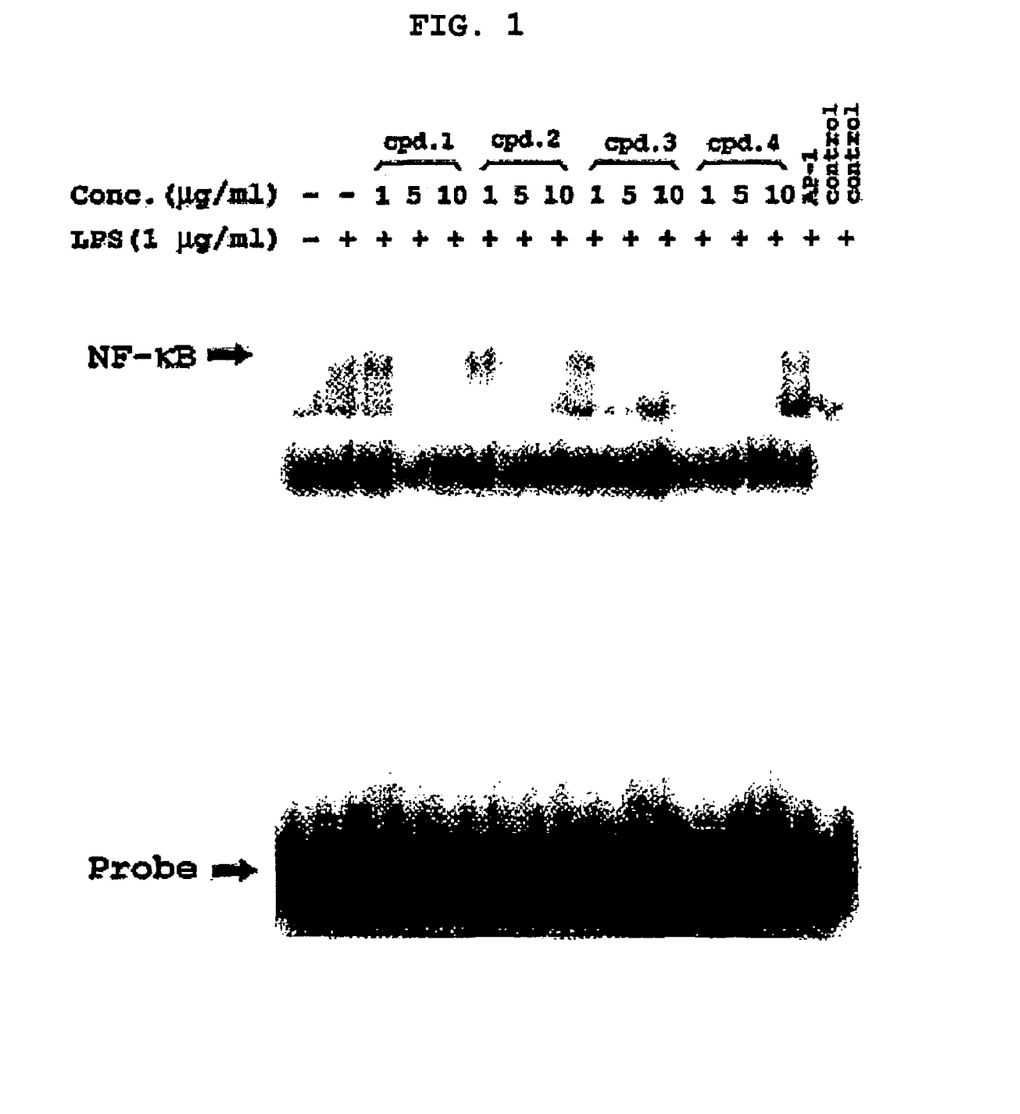
FIG. 1 shows the result of measuring inhibitory effect of kamebanin, kamebacetal A, kamebakaurin, and exisanin A, each of which is a member of the kaurane diterpene compounds, on the NF-κB (nuclear factor Kappa B) activation.

As a result, as is shown in FIG. 1, DNA binding activity of NF-κB induced by LPS was decreased dose-dependently by the treatment of kaurane diterpene compounds of the present invention. Especially, when 10 mg/ml concentrations of each compound were treated, DNA binding activity of NF-κB was completely suppressed.

In the FIG. 1, cpd. 1 corresponds to kamebanin, cpd. 2 corresponds to kamebacetal A, cpd. 3 corresponds to kamebakaurin and cpd.4 corresponds to exisanin A.

From this result, it is found that kaurane diterpene compounds of the present invention inhibit the DNA binding activity of NF-κB, which plays a central role in the expression of the inflammatory mediators and antiapoptotic proteins inhibiting apoptosis of cancer cells, ensuring that these compounds can be useful as therapeutic agents for inflammatory diseases, immunological diseases and cancer.

Example 6

Anti-inflammatory Effect of Kaurane Diterpene Compound

Finding the inhibitory effect of kaurane diterpene compounds on the production of NO, prostaglandin, and TNF, and on the activation of NF-κB in the murine macrophage cells stimulated by LPS, the present inventors investigated the pharmacological efficacy of kaurane diterpene compounds with a adjuvant arthritis model according to the method of Futaki et al. (*General Pharmacology*, 1993, 24, 105–110).

To prepare animal model of the arthritis, 0.05 ml of 0.1% *Mycobacterium butyricum* suspended in Freud adjuvant (Sigma, USA) was injected intradermally to the left hind paw of the male Sprague-Dawley rat of 180 g weight. On the fifteenth day after injection, the volume of the right paw of the rats was measured using plethysmometer (Ugo-Basile, Italy), and only the rats having arthritis on the right leg were selected.

Thereafter, the selected rats were divided into four groups, six rats per each group. Four kinds of kaurane diterpene compounds of the present invention were administered orally to each groups everyday from the sixteenth day to twenty-second day with doses of 3 mg/kg/day, 10 mg/kg/day, and 20 mg/kg/day in the form of the suspended solution with 0.1% methylcellulose. The inhibition rate of arthritis was calculated by comparing the volume of the paw with that of the control on the $23^{rd}$ day. Table 5 shows the result.

TABLE 5

Anti-inflammatory effect of kaurane diterpene compounds

| Compounds | Dose (oral administration) | Inhibition rate (%) |
| --- | --- | --- |
| Kamebanin | 3 mg/kg/day | 30 ± 15 |
| | 10 mg/kg/day | 50 ± 12 |
| | 20 mg/kg/day | 68 ± 14 |
| Kamebacetal A | 3 mg/kg/day | 33 ± 18 |
| | 10 mg/kg/day | 55 ± 10 |
| | 20 mg/kg/day | 69 ± 14 |
| Kamebakaurin | 3 mg/kg/day | 35 ± 19 |
| | 10 mg/kg/day | 59 ± 11 |
| | 20 mg/kg/day | 71 ± 17 |
| Exisanin A | 3 mg/kg/day | 33 ± 14 |
| | 10 mg/kg/day | 52 ± 12 |
| | 20 mg/kg/day | 64 ± 13 |

As is shown in Table 5, arthritis was suppressed dose-dependently by the treatment of kaurane diterpene compounds of the present invention. From these results, the possibility for the compounds to be used as anti-inflammatory agent was ensured.

Example 7

Inhibitory Effect of Kaurane Diterpene Compounds on the Expression of the Anti-apoptotic Gene To investigate the effect of the kaurane diterpene compounds of the present invention on the expression of the anti-apoptotic proteins such as Bf1-1/A1, cIAP-1, and cIAP-2, the present inventors performed the following experiments.

<7-1> Effect of the Kaurane Diterpene Compounds on the Expression of the Bf1-1/A1 mRNA MCF-7 cells (ATCC HTB 22, breast cancer cell line) and HT-1080 cells (ATCC CCL 121, fibroblastoma) were pretreated for 30 minutes with 1 μg/ml, 5 μg/ml, and 10 μg/ml concentrations of four kinds of kaurane diterpene compounds. Thereafter, 20 ng/ml concentrations of TNF-α were treated for three hours to induce the expression of Bf1-1/A1 mRNA. After isolating total RNA from the control and compound-treated cells, the expression of Bf1-1/A1 mRNA was measured by Northern blot analysis. To accomplish this, 20 μg of the total RNA was electrophoresed in the 1% agarose gel containing 2.2M concentrations of formaldehyde. After that, RNA was transferred to nylon membrane and fixed using ultraviolet. The nylon membrane was hybridized with $^{32}$P-labeled probe, which was represented by SEQ. ID NO. 2 and specific to the cDNA of Bf1-1/A1 gene. After washing unbound probe with phosphate buffered saline (PBS) containing sodium dodecyl sulfate (SDS), the membrane was exposed to x-ray film.

As a result, the amount of extracted total RNA was constant in the sample and control groups. The expression level of the Bf1-1/A1 mRNA induced by TNF-α, was inhibited dose-dependently by the treatment of kaurane diterpene compounds of the present invention. The result using kamebakaurin was shown in FIG. 2a. FIG. 2a (1) shows the inhibitory effect on the expression of Bf1-1/A1 mRNA in MCF-7 cells, and FIG. 2a (2) shows the inhibitory effect on the expression of Bf1-1/A1 mRNA in HT1080 cells.

<7-2> Effect of the Kaurane Diterpene Compounds on the Expression of the cIAP-1 and cIAP-2 Proteins MCF-7 cells and HT-1080 cells were pretreated for 30 minutes with 1 μg/ml, 5 μg/ml, and 10 μg/ml concentrations of four kinds of kaurane diterpene compounds, respectively. After that, 20 ng/ml concentrations of TNF-α were treated for three hours to induce the expression of cIAP-1 and cIAP-2 proteins. Protein extract was prepared from cultured cells using buffer solution for protein extraction consisting of 50 mM Tris-HCL (pH 7.5), 1% Nonidet P40, 150 mM NaCl, 1 mM EDTA, 1 mM phenylmethyl sulfonyl fluoride, 2 g/ml leupeptin, and 2 g/ml aprotinin. 50 μg of protein extract of the control and compound-treated groups was applied to the SDS-polyacrylamide gel electrophoresis. After transferring the proteins into the polyvinylidene difluoride membrane, the membrane was blocked with 5% skim milk for three hours, and were reacted with antibodies against cIAP-1, cIAP-2, Bcl-2, and Bax proteins (Santa Cruz Biochemicals). The membrane was washed with PBS and was reacted with secondary antibody conjugated with horseradish peroxidase. After washing again with PBS, the protein was detected by ECL system (Amersham Pharmacia Biotec).

As a result, the expression of cIAP-1 and cIAP-2 proteins, which was regulated by NF-κB and induced by TNF-α, were inhibited dose-dependently by the treatment of kaurane diterpene compounds of the present invention. However, the treatment of kaurane diterpene compounds did not influence the expression of anti-apoptotic protein, Bcl-2, and proapoptotic protein, Bax. The result using kamebakaurin was shown in FIG. 2b.

From these results, it was found that kaurane diterpene compounds of the present invention inhibited the TNF-α-induced expression of c-IAP-1, c-IAP-2, and Bf1-1/A1 genes, ensuring the possibility for the compounds to be used as auxiliary agents in the chemotherapy and radiation therapy for cancer.

Example 8

Acute Toxicity Test of Kaurane Diterpene Compounds in Rats Via Oral Administration The following experiments were performed to see if kaurane diterpene compounds of the present invention have acute toxicity in rats. Six-week old specific-pathogen free (SPF) SD line rats were used in the tests for acute toxicity. Kaurane diterpene compounds of the present invention were suspended in 0.5% methylcellulose solution and orally administered once to six rats per group at the dosage of 0.5 g/kg/15 ml. Death, clinical symptoms, and weight change in the tested animals were observed. In addition, hematological and biochemical tests of blood were performed, and any abnormal signs in the gastrointestinal organs of chest and abdomen were checked visually (with the naked eye) during autopsy.

The results showed that the tested compounds did not cause any specific clinical symptoms, weight changes, or death in rats, except in the cases of kamebanin, in which toxicity was seen in hematological testing, biochemical testing, and visual observation. No change was observed in hematological tests, biochemical tests of blood, and autopsy in cases using kamebacetal A, kamebakaurin, and exisanin A. Therefore, the compounds used in this experiment are evaluated to be safe substances, since they do not cause any toxic change in rats up to the level of 0.5 g/kg and their estimated $LD_{50}$ values are much greater than 0.5 g/kg in rats.

Example 9

Inhibitory Effect of Kaurane Diterpene Compounds on the Expression of iNOS and COX-2

The production of NO and prostaglandin, both are induced by LPS treatment in Raw 264.7 murine macrophage cell, is dependent on the.expression of iNOS and COX-2 proteins, respectively. Therefore, the present inventors investigated the effect of kamebakaurin on the expression of INOS and COX-2 proteins by the following experiments.

<9-1> Effect of Kaurane Diterpene Compounds on the Expression of the iNOS and COX-2 mRNA Raw 264.7 murine macrophage cells were treated simultaneously with 1 μg/ml concentrations of LPS and 0.1 μg/ml, 0.3 μg/ml, 1 μg/ml, and 3 μg/ml concentrations of kamebakaurin and were incubated for 6 hours at 37° C. in a 5% $CO_2$ incubator. After isolation of total RNA, reverse transcriptase-polymerase chain reaction (RT-PCR) was performed using said RNA as a template and primer pairs represented by SEQ. ID NO. 3 and 4 for iNOS gene and primer pairs represented by SEQ. ID NO. 5 and 6 for COX-2.

As a result, as was shown in FIG. 3a, the expression of INOS and COX-2 mRNA was suppressed by the treatment of kamebakaurin. Especially, the expression of iNOS mRNA was completely suppressed by the treatment of 1 μg/ml concentrations of kamebakaurin and that of COX-2 mRNA was completely suppressed by the treatment of 3 μg/ml concentrations of kamebakaurin.

<9-2> Effect of Kaurane Diterpene Compounds on the Expression of the iNOS and COX-2 Proteins Raw 264.7 murine macrophage cells were treated simultaneously with 1 μg/ml concentrations of LPS and 0.1 μg/ml, 0.3 μg/ml, 1 μg/ml, and 3 μg/ml concentrations of kamebakaurin and were incubated for 18 hours at 37° C. in a 5% $CO_2$ incubator. After preparing total cell lysates from cultured cells using buffer solution for protein extraction of the Example <7-2>, the expression pattern of proteins was assessed by Western blot analysis.

Figure 3B:
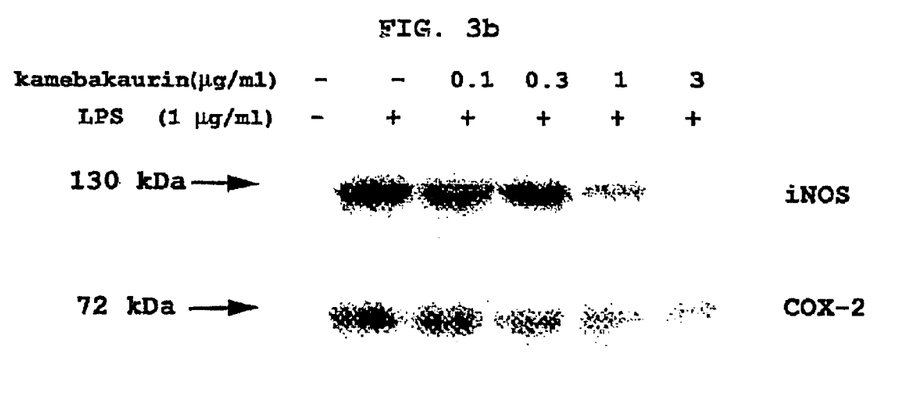
FIG. 3b shows the result of Western blot analysis showing the inhibition of the protein expression of iNOS and COX-2 by kamebakaurin, one of the kaurane diterpene compound of the present invention.

As a result, iNOS protein of 130 kDa and COX-2 protein of 72 kDa induced by the treatment of LPS were detected in control group which was not treated with kamebakaurin, whereas the expression of the proteins was suppressed dose-dependently by the treatment of kamebakaurin in sample group treated with kamebakaurin. Especially, the expression of iNOS protein was completely suppressed by the treatment of 3 μg/ml concentrations of kamebakaurin (FIG. 3b).

From these results, it was found that kamebakaurin inhibited specifically the activity of iNOS and COX-2 proteins, ensuring the use of kamebakaurin as an inhibitor in the production of proinflammatory agents, such as NO and prostaglandin.

Example 10

Effect of Kamebakaurin on the Potentiation of Cytotoxicity Induced by TNF-α

To investigate the effect of kamebakaurin on the cytotoxicity induced by TNF-α, the following experiment was performed.

In detail, MCF-7 cells were suspended in DMEM medium, seeded to a 96-well plate at concentrations of $1 \times 10^4$ cells/well, and incubated for 24 hours at 37° C. in a 5% $CO_2$ incubator. After preincubation with 1 μg/ml and 5 μg/ml concentrations of kamebakaurin for 30 minutes, 20 ng/ml concentrations of TNF-α was added to each well. After incubating the cells for 48 hours, 3-(4,5-dimethylthiazol-2-yl)-2,5-diphenyltetrazolium bromide (MTT) was added to the cells for four hours. Formazan dye thus formed was dissolved in dimethylsulfoxide and the amount of it was measured by absorbance at 570 nm wavelength.

As a result, as was shown in FIG. 4, cell viability was decreased up to 85% by the treatment of TNF-α alone. In contrast, cell viability was decreased up to 20%, and 15% by co-treatment of kamebakaurin and TNF-α, indicating that kaurane diterpenes potentiated TNF-α-induced cytotoxicity. (The asterisk in FIG. 4 indicates that the values have statistical significance.) From above results, it was found that the treatment of diterpene compounds such as kamebakaurin of the present invention ptentiated TNF-α-induced cytotoxicity against cancer cells, ensuring the possibility for the compound to be used as an auxiliary agent in the chemotherapy and radiation therapy for cancer.

INDUSTRIAL APPLICABILITY

As described above, kaurane diterpene compounds such as kamebanin, kamebacetal A, kamebakaurin, and exisanin A inhibited the activation of NF-κB, an important factor in the expression of proinflammatory cytokines, inflammatory enzymes, and adhesion molecules, resulting in strong inhibition of the production of NO, prostaglandin, and TNF, and were proved to be safe in a acute toxicity test in rats. Especially, kamebakaurin was proved to inhibit the expression antiapoptotic proteins such as Bf1-1/A1, cIAP-1, and cIAP-2, and to have excellent anti-inflammatory activity in arthritis animal model. Therefore, kaurane diterpene compounds of the present invention are useful not only as a therapeutic agent against the inflammatory diseases such as arthritis and septic shock, autoimmune diseases, and diseases related to the death of neuron cells, but also as an auxiliary agent in the chemotherapy and radiation therapy for cancer.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A method of treating inflammatory disease or immunological disease, comprising administering a therapeutically effective amount of kamebanin according to formula 1

Formula 1 to a patient in need thereof.

2. A method of treating inflammatory disease or immunological disease, comprising administering a therapeutically effective amount of kamebacetal A according to formula 2

Formula 2 to a patient in need thereof.

3. A method of treating inflammatory disease or immunological disease, comprising administering a therapeuti- cally effective amount of kamebakaurin according to formula 3

Formula 3 to a patient in need thereof.

4. A method of treating inflammatory disease or immunological disease, comprising administering a therapeutically effective amount of exisanin A according to formula 4

Formula 4 to a patient in need thereof.

5. A method of treating cancer, comprising administering a therapeutically effective amount of kamebanin according to formula 1

Formula 1 to a patient in need thereof.

6. A method of treating cancer, comprising administering a therapeutically effective amount of kamebacetal A according to formula 2

Formula 2 to a patient in need thereof.

7. A method of treating cancer, comprising administering a therapeutically effective amount of kamebakaurin according to formula 3

Formula 3 to a patient in need thereof.

* * * * *

SEQUENCE LISTING

```
<160> NUMBER OF SEQ ID NOS: 6

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: NF-?B
      double strand oligonucleotide

<400> SEQUENCE: 1
agttgagggg actttcccag gc                                              22

<210> SEQ ID NO 2
<211> LENGTH: 737
<212> TYPE: DNA
<213> ORGANISM: Artificial Sequence
<220> FEATURE:
<223> OTHER INFORMATION: Description of Artificial Sequence: Bfl-a/A1
      cDNA nucleotide sequences

<400> SEQUENCE: 2
ccagctcaag actttgctct ccaccaggca gaagatgaca gactgtgaat ttggatatat     60
ttacaggctg gctcaggact atctgcagtg cgtcctacag ataccacaac ctggatcagg    120
tccaagcaaa acgtccagag tgctacaaaa tgttgcgttc tcagtccaaa aagaagtgga    180
aaagaatctg aagtcatgct tggacaatgt taatgttgtg tccgtagaca ctgccagaac    240
actattcaac caagtgatgg aaaaggagtt tgaagacggc atcattaact ggggaagaat    300
tgtaaccata tttgcatttg aaggtattct catcaagaaa cttctacgac agcaaattgc    360
cccggatgtg gatacctata aggagatttc atattttgtt gcggagttca taatgaataa    420
cacaggagaa tggataaggc aaaacggagg ctgggaaaat ggctttgtaa agaagtttga    480
acctaaatct ggctggatga cttttctaga agttacagga aagatctgtg aaatgctatc    540
tctcctgaag caatactgtt gaccagaaag gacactccat attgtgaaac cggcctaatt    600
tttctgactg atatggaaac gattgccaac acatacttct acttttaaat aaacaacttt    660
gatgatgtaa cttgaccttc cagagttatg gaaattttgt ccccatgtaa tgaataaatt    720
gtatgtattt ttctcta                                                   737

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: iNOS sense
      primers

<400> SEQUENCE: 3
cagaagcaga atgtgaccat c                                               21

<210> SEQ ID NO 4
<211> LENGTH: 21
<212> TYPE: DNA
<213> ORGANISM: Artificial Sequence
<220> FEATURE:
```

```
<223> OTHER INFORMATION: Description of Artificial Sequence: iNOS
      antisense primers

<400> SEQUENCE: 4
cttctggtcg atgtcatgag c                                             21

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: COX-2 sense
      primers

<400> SEQUENCE: 5
actcactcag tttgttgagt cattc                                         25

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: COX-2
      antisense primers

<400> SEQUENCE: 6
tttgattagt actgtagggt taatg                                         25
```